United States Patent
Numazu

(10) Patent No.: US 9,194,814 B2
(45) Date of Patent: Nov. 24, 2015

(54) GLASS BOTTLE INSPECTION APPARATUS AND METHOD

(75) Inventor: Masaaki Numazu, Kawasaki (JP)

(73) Assignee: KIRIN TECHNO-SYSTEM COMPANY, LIMITED, Kanagawa (JP)

(*) Notice: Subject to any disclaimer, the term of this patent is extended or adjusted under 35 U.S.C. 154(b) by 368 days.

(21) Appl. No.: 13/877,116

(22) PCT Filed: Sep. 28, 2011

(86) PCT No.: PCT/JP2011/072163
§ 371 (c)(1),
(2), (4) Date: May 7, 2013

(87) PCT Pub. No.: WO2012/043618
PCT Pub. Date: Apr. 5, 2012

(65) Prior Publication Data
US 2013/0222575 A1    Aug. 29, 2013

(30) Foreign Application Priority Data
Oct. 1, 2010 (JP) .................................. 2010-223477

(51) Int. Cl.
*G01N 21/90* (2006.01)
(52) U.S. Cl.
CPC ........ *G01N 21/9036* (2013.01); *G01N 21/9054* (2013.01)
(58) Field of Classification Search
CPC ....................................................... G01N 21/90
USPC ................................................. 348/127, 123
See application file for complete search history.

(56) References Cited

U.S. PATENT DOCUMENTS

| | | | |
|---|---|---|---|
| 3,454,712 A * | 7/1969 | Mottram | 348/123 |
| 5,900,945 A | 5/1999 | Hinata et al. | |
| 6,275,287 B1 * | 8/2001 | Watanabe | 356/239.4 |
| 6,480,280 B1 | 11/2002 | Hinata | |
| 6,512,239 B1 * | 1/2003 | Weiss et al. | 250/559.4 |
| 6,643,009 B2 * | 11/2003 | Takakusaki et al. | 356/240.1 |
| 6,903,814 B1 * | 6/2005 | Juvinall et al. | 356/240.1 |
| 7,005,629 B2 * | 2/2006 | Flem | 250/223 B |
| 2007/0225560 A1 * | 9/2007 | Avni et al. | 600/118 |

(Continued)

FOREIGN PATENT DOCUMENTS

| | | |
|---|---|---|
| JP | 4-294262 A | 10/1992 |
| JP | 9-119902 A | 5/1997 |
| JP | 10-82624 A | 3/1998 |
| JP | 11-108854 A | 4/1999 |

(Continued)

*Primary Examiner* — Paulos M Natnael
(74) *Attorney, Agent, or Firm* — Sughrue Mion, PLLC

(57) ABSTRACT

The present invention relates to a glass bottle inspection apparatus which can detect a defect at a specific location such as a bottle-mouth portion of a glass bottle by an imaging process. The glass bottle inspection apparatus includes an inspection unit having one or plural illuminating units (LED1 through LED6) configured to illuminate a glass bottle (1) and at least one camera (CAM1 through CAM4) configured to image light reflected from the glass bottle (1), configured to detect a defect at a specific location of the glass bottle. The apparatus has a controller (4) configured to control operations of the one or plural illuminating units (LED1 through LED6) and the camera (CAM1 through CAM4). The controller (4) controls the one or plural illuminating units (LED1 through LED6) individually to emit a pulsed light in synchronism with an image capturing timing of the camera (CAM1 through CAM4).

12 Claims, 10 Drawing Sheets

(56) References Cited

U.S. PATENT DOCUMENTS

| | | | |
|---|---|---|---|
| 2008/0093538 A1* | 4/2008 | Diehr et al. | 250/223 B |
| 2008/0095427 A1* | 4/2008 | Novini et al. | 382/142 |
| 2008/0116358 A1 | 5/2008 | Diehr et al. | |
| 2012/0249862 A1* | 10/2012 | Makino | 348/362 |

FOREIGN PATENT DOCUMENTS

| | | |
|---|---|---|
| JP | 11-344451 A | 12/1999 |
| JP | 2004-271205 A | 9/2004 |
| JP | 2008-107348 A | 5/2008 |
| JP | 4478786 B2 | 6/2010 |

* cited by examiner

GLASS BOTTLE INSPECTION APPARATUS AND METHOD

CROSS REFERENCE TO RELATED APPLICATIONS

This application is a National Stage of International Application No. PCT/JP2011/072163 filed Sep. 28, 2011, the contents of which are incorporated herein by reference in their entirety.

TECHNICAL FIELD

The present invention relates to a glass bottle inspection apparatus and method, and more particularly to a glass bottle inspection apparatus and method for detecting a defect at a specific location of a bottle-mouth portion and the like of a glass bottle by an imaging process.

BACKGROUND ART

In producing a glass bottle, a crack such as crazing may be sometimes formed in a wall thickness of a bottle-mouth portion. This crack is referred to as a check. Some glass bottles are manufactured as returnable bottles that are retrieved for reuse after they have been used. Returnable bottles are likely to have checks at their bottle-mouth portions when they are brought into contact with each other or with other objects while in use or transport. Glass bottles, regardless of whether they are newly produced bottles or returnable bottles, tend to have checks in limited regions of the bottle-mouth portions. Typically, there are a check generated in the top surface or near the top surface of the bottle mouth, a check generated in a screw thread portion of the bottle mouth, and a check generated in a skirt portion of the bottle mouth. Further, depending on the direction of the crack, the checks are classified into a vertical check extending in a vertical direction (substantially vertical direction) and a lateral check extending in a lateral direction (substantially horizontal direction).

Because the above-mentioned check can cause damage to the glass bottle, the presence or absence of a check is detected by imaging the bottle-mouth portion, and the glass bottle having the check is removed as a defective bottle.

Heretofore, there has been known a glass bottle inspection apparatus for automatically inspecting a glass bottle by imaging a bottle-mouth portion of a glass bottle to detect whether there is a check or not. The known glass bottle inspection apparatus has a single illuminating unit disposed above the bottle-mouth portion of a glass bottle and a number of (e.g., seven) cameras disposed around the bottle-mouth portion so as to surround the bottle-mouth portion. Scattered light emitted from the illuminating unit is applied to the bottle-mouth portion of the glass bottle, and if there is a check, the light is reflected by a crack plane of the check and is thus illuminated brightly. Therefore, images captured by the cameras include a brighter image area corresponding to the check than other image areas. The brighter image area is detected by image processing and judged as a check.

CITATION LIST

Patent Literature

Patent document 1: Japanese patent No. 4478786

SUMMARY OF INVENTION

Technical Problem

As described above, the process of inspecting the bottle-mouth portion of the glass bottle is performed using the cameras to detect a check by capturing an image of the light reflected from the crack plane of the check. The direction in which the reflected light travels depends on the direction of the crack plane of the check, and hence varies from check to check. If the number of illuminating units per a camera is increased, the detection accuracy for detecting checks is enhanced. However, lights emitted from the plural illuminating units tend to interfere with each other.

Since the conventional glass bottle inspection apparatus employs a number of (e.g., seven) cameras, it requires a large installation space for the cameras. As the cameras are more expensive than other components such as an illuminating unit, they are responsible for an increase in the cost of the glass bottle inspection apparatus.

The present invention has been made in view of the above drawbacks. It is therefore an object of the present invention to provide a glass bottle inspection apparatus and method which can enhance inspection accuracy by increasing the number of illuminating units and can lower the cost by reducing the number of cameras.

Solution to Problem

In order to achieve the above object, according to the present invention, there is provided a glass bottle inspection apparatus, having an inspection unit which comprises one or plural illuminating units configured to illuminate a glass bottle and at least one camera configured to image light reflected from the glass bottle, configured to detect a defect at a specific location of the glass bottle, the glass bottle inspection apparatus comprising: a controller configured to control operations of the one or plural illuminating units and the camera; wherein the controller controls the one or plural illuminating units individually to emit a pulsed light in synchronism with an image capturing timing of the camera.

According to the present invention, there is provided a glass bottle inspection method of detecting a defect at a specific location of a glass bottle by using an inspection unit which comprises one or plural illuminating units configured to illuminate the glass bottle and at least one camera configured to image light reflected from the glass bottle, the glass bottle inspection method comprising: controlling the one or plural illuminating units individually to emit a pulsed light in synchronism with an image capturing timing of the camera.

According to the glass bottle inspection apparatus and method of the present invention, one illuminating unit is turned on to emit a pulsed light at the same timing as an image capturing timing of the camera, and then another illuminating unit is turned on to emit a pulsed light at the same timing as a next image capturing timing of the camera. In this manner, the illuminating units are individually turned on to emit pulsed lights in synchronism with image capturing timings of the camera. Consequently, the number of illuminating units can be increased with respect to one camera, and thus the detection accuracy of checks can be increased. Even if the number of illuminating units is increased with respect to one camera, the lights emitted from the illuminating units do not interfere with each other.

The pulsed light is a light emitted from an illuminating unit by supplying a pulsed current to the illuminating unit to repeat turning-on and turning-off of the illuminating unit at intervals.

In a preferred aspect of the present invention, the one or plural illuminating units and the camera are disposed in respective positions which are substantially opposite to each other across the glass bottle.

According to the present invention, the one or plural illuminating units and the camera are disposed in respective positions which are substantially opposite to each other to illuminate the glass bottle by the pulsed light from the illuminating unit and to allow the light reflected from the glass bottle to reach the camera.

In a preferred aspect of the present invention, the defect in the specific location of the glass bottle comprises a check in a bottle-mouth portion of the glass bottle, the one or plural illuminating units are disposed obliquely upwardly or laterally of the bottle-mouth portion of the glass bottle, and the camera is disposed obliquely upwardly or laterally of the bottle-mouth portion.

According to the present invention, the light from the illuminating unit is applied to the bottle-mouth portion of the glass bottle. If there is a check in the bottle-mouth portion, the light applied to the bottle-mouth portion is reflected by the crack plane of the check, and the reflected light is imaged by the camera. In an image captured by the camera, an image area corresponding to the check appears as a brighter image area than other image areas. An image processor of the controller processes the image, detects the brighter image area, and judges the brighter image area as a check.

In a preferred aspect of the present invention, the glass bottle inspection apparatus further comprises a bottle support configured to support the glass bottle in an erected state and configured to rotate the glass bottle about its own axis.

According to the present invention, when the bottle support is rotated about its own axis, the glass bottle is rotated about its own axis. While the glass bottle makes one revolution, the bottle-mouth portion is imaged fully circumferentially by the camera. A number of captured images are successively processed by the image processor of the controller, and the full circumference of a top surface of the bottle-mouth portion and the full circumference of a bottle side face including a thread and a skirt are inspected for detecting checks based on the processed images.

In a preferred aspect of the present invention, the inspection unit comprises a plurality of inspection units disposed at different angular positions so as to surround the bottle-mouth portion of the glass bottle.

According to the present invention, since the plural inspection units are disposed at different angular positions, they can be positioned without physical interference with each other.

In a preferred aspect of the present invention, the plural inspection units are capable of detecting checks having different crack planes.

According to the present invention, since the plural inspection units can detect checks having different crack planes, they can detect checks in the vicinity of the top surface of bottle mouth, vertical checks whose crack planes extend in a vertical direction (substantially vertical direction), and lateral checks whose crack planes extend in a lateral direction (substantially horizontal direction).

In a preferred aspect of the present invention, the plural inspection units include respective cameras having different image capturing timings.

According to the present invention, since the inspection units include respective cameras having different image capturing timings, and a plurality of illuminating units of each inspection unit are turned on to emit pulsed lights at different timings in synchronism with image capturing timings of one camera, the plural illuminating units can individually be turned on to emit pulsed lights in synchronism with image capturing timings of the camera in each of the inspection units which include the plural cameras and the plural illuminating units.

In a preferred aspect of the present invention, the defect at the specific location of the glass bottle comprises a blister in a bottle-mouth portion of the glass bottle, one of the plural illuminating units comprises an illuminating unit dedicated for inspection of blisters which is disposed above the bottle-mouth portion, and the camera is disposed obliquely upwardly or laterally of the bottle-mouth portion.

According to the present invention, the light from the illuminating unit dedicated for inspection of blisters is applied to a blister and reflected and scattered therefrom in various directions. The light reflected and scattered from the blister is applied to and captured by the camera that is disposed obliquely upwardly or laterally of the bottle-mouth portion. In an image captured by the camera, an image area corresponding to the blister appears as a brighter image area than other image areas. The image processor of the controller processes the image, detects the brighter image area, and judges the brighter image area as a blister.

In a preferred aspect of the present invention, the defect at the specific location of the glass bottle comprises a blister in a bottle-mouth portion of the glass bottle, one of the plural illuminating units comprises an illuminating unit dedicated for inspection of blisters, and the controller detects a blister from an image captured by the at least one camera while the illuminating unit dedicated for inspection of blisters is turned on to emit a pulsed light, masks and removes an image area corresponding to the blister from an inspection area of the image captured by the at least one camera while the illuminating units other than the illuminating unit dedicated for inspection of blisters are turned on to emit pulsed lights, and detects a check defect from the remaining inspection area.

According to the present invention, the captured images are successively processed by the image processor of the controller. If there is a brighter image area in a dark background in the image captured by the camera while the illuminating unit dedicated for inspection of blisters is turned on to emit a pulsed light, the image processor detects and judges the brighter image area as a blister. Thereafter, the image processor masks and removes an image area corresponding to the blister from an inspection area of the image captured by the camera while the illuminating units other than the illuminating unit dedicated for inspection of blisters are turned on to emit pulsed lights. If there is a brighter image area in the remaining inspection area, then the image processor detects and judges the brighter image area as a check defect.

Advantageous Effects of Invention

The present invention offers the following advantages:

(1) Since one or plural illuminating units are individually turned on to emit a pulsed light in synchronism with image capturing timings of the camera, the number of illuminating units can be increased with respect to one camera, and thus the detection accuracy of checks can be enhanced. Even if the number of illuminating units is increased with respect to one camera, the lights emitted from the illuminating units do not interfere with each other.

(2) The number of cameras can be reduced compared with the conventional inspection apparatus. Therefore, the cost of the inspection apparatus can be reduced, and the installation space of cameras can be reduced.

(3) A blister can be detected from the image captured by the camera while the illuminating unit dedicated for inspection of blisters is turned on to emit a pulsed light, and an image area corresponding to the position of the blister can be masked and removed from an inspection area of the image captured by the camera while other illuminating units than the illuminating unit dedicated for inspection of blisters are turned on to emit pulsed lights. Therefore, only a check defect can be detected from the captured images. Accordingly, a blister and a check can be detected distinguishably from each other.

DESCRIPTION OF EMBODIMENTS

A glass bottle inspection apparatus and method according to embodiments of the present invention will be described below with reference to FIGS. 1 through 10. In the glass bottle inspection apparatus and method according to embodiments of the present invention, the bottle-mouth portion of a glass bottle will be described as a specific location of the glass bottle to be inspected, and a check in the bottle-mouth portion will be described as a defect to be inspected.

A glass bottle to be inspected is held by an inspection star wheel (not shown) and is conveyed along a conveyance path on a circumference of the star wheel. The glass bottle inspection apparatus according to the present invention is disposed in one inspecting station at a certain place in the conveyance path on the circumference of the star wheel. The glass bottle conveyed by the start wheel is indexed to the inspecting station, where the presence or absence of a check in the bottle-mouth portion of the glass bottle is inspected by the glass bottle inspection apparatus according to the present invention.

Figure 1:
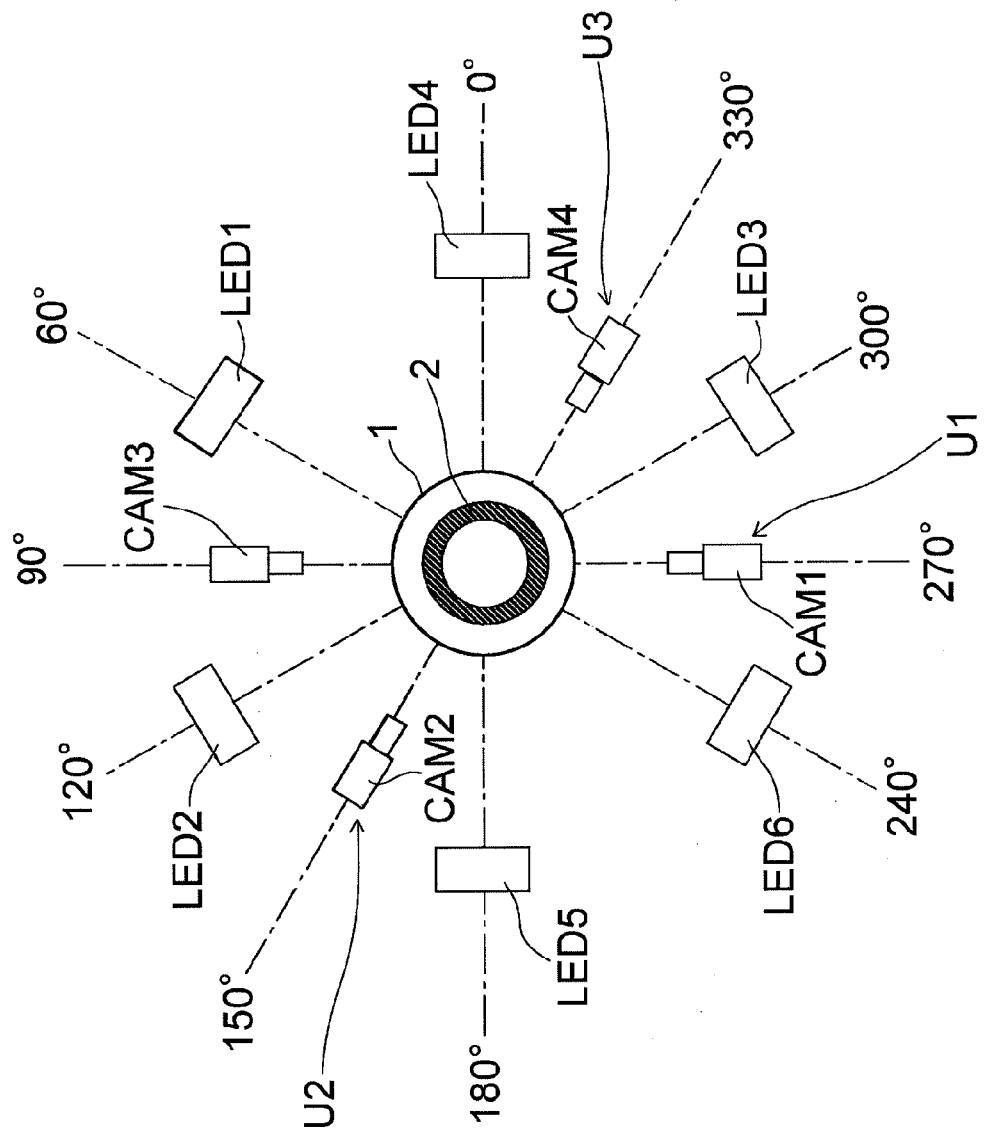
FIG. 1 is a plan view of a glass bottle inspection apparatus.

FIG. 1 is a plan view of the glass bottle inspection apparatus. As shown in FIG. 1, the glass bottle inspection apparatus has three inspection units U1, U2, U3 disposed around the bottle-mouth portion 2 of a glass bottle 1. The bottle-mouth portion 2 is shown by oblique lines in FIG. 1. The first inspection unit U1 comprises two illuminating units LED1, LED2 and a single camera CAM1. The illuminating unit LED1 is disposed in an angular position of 60°, the illuminating unit LED2 in an angular position of 120°, and the camera CAM1 in an angular position of 270°. The second inspection unit U2 comprises two illuminating units LED3, LED4 and a single camera CAM2. The illuminating unit LED3 is disposed in an angular position of 300°, the illuminating unit LED4 in an angular position of 0°, and the camera CAM2 in an angular position of 150°. The third inspection unit U3 comprises two illuminating units LED5, LED6 and two cameras CAM3, CAM4. The illuminating unit LED5 is disposed in an angular position of 180°, the illuminating unit LED6 in an angular position of 240°, the camera CAM3 in an angular position of 90°, and the camera CAM4 in an angular position of 330°. Each of the illuminating units LED1 through LED6 comprises a red LED, and each of the cameras CAM1 through CAM4 comprises a CCD camera.

Figure 2:
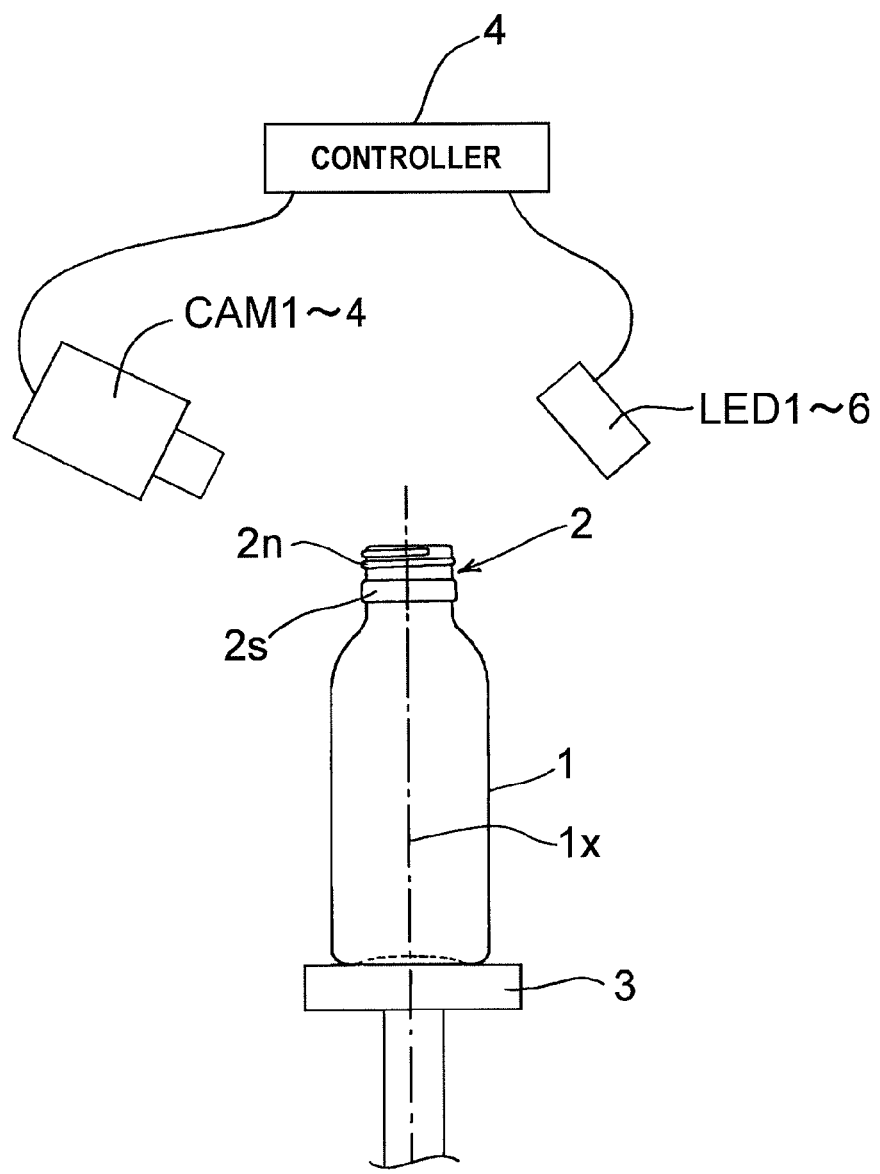
FIG. 2 is a schematic view showing a basic arrangement of the glass bottle inspection apparatus shown in FIG. 1.

FIG. 2 is a schematic view showing a basic arrangement of the glass bottle inspection apparatus shown in FIG. 1. The illuminating units LED1 through LED6 and the cameras CAM1 through CAM4, which are positioned in the layout shown in FIG. 1, are illustrated not individually, but collectively in FIG. 2.

As shown in FIG. 2, the glass bottle 1 is placed on a bottle support 3. When the bottle support 3 is rotated about its own axis, the glass bottle 1 is rotated about its own axis $1x$. The bottle-mouth portion 2 of the glass bottle 1 has a thread $2n$ and a skirt $2s$ below the thread $2n$. The illuminating units LED1 through LED6 are disposed obliquely upwardly or laterally of the bottle-mouth portion 2 of the glass bottle 1. The cameras CAM1 through CAM4 are disposed obliquely upwardly or laterally of the bottle-mouth portion 2 of the glass bottle 1.

The illuminating units LED1 through LED6 and the cameras CAM1 through CAM4 are connected to a controller 4. The illuminating units LED1 through LED6 are controlled by the controller 4 to emit successive pulsed lights, and the cameras CAM1 through CAM4 are controlled by the controller 4 to capture successive images of the bottle-mouth portion 2. Specifically, while one of the illuminating units LED1 through LED6, e.g., the illuminating unit LED1, is turned on to emit a pulsed light, the other illuminating units LED2 through LED6 are not turned on. While the next illuminating unit LED2 is turned on to emit a pulsed light, the other illuminating units LED1, LED3 through LED6 are not turned on. In this manner, the illuminating units LED3 through LED6 are successively turned on subsequently. The illuminating units LED1 through LED6 are turned on to emit pulsed lights in synchronism with the image capturing timings of the cameras CAM1 through CAM4. Specifically, the illuminating unit LED1 is turned on to emit a pulsed light at the same timing as the image capturing timing of the camera CAM1, and then the illuminating unit LED2 is turned on to emit a pulsed light at the same timing as the image capturing timing of the camera CAM1. Thereafter, the illuminating unit LED3 is turned on to emit a pulsed light at the same timing as the image capturing timing of the camera CAM2, and then the illuminating unit LED4 is turned on to emit a pulsed light at the same timing as the image capturing timing of the camera CAM2. Thereafter, the illuminating unit LED5 is turned on to emit a pulsed light at the same timing as the image capturing timing of the camera CAM3, and then the illuminating unit LED6 is turned on to emit a pulsed light at the same timing as the image capturing timing of the camera CAM4. The controller 4 includes an image processor for processing images captured by the cameras CAM1 through CAM4. Therefore, the images captured by the cameras CAM1 through CAM4 are processed by the image processor.

Figure 3:
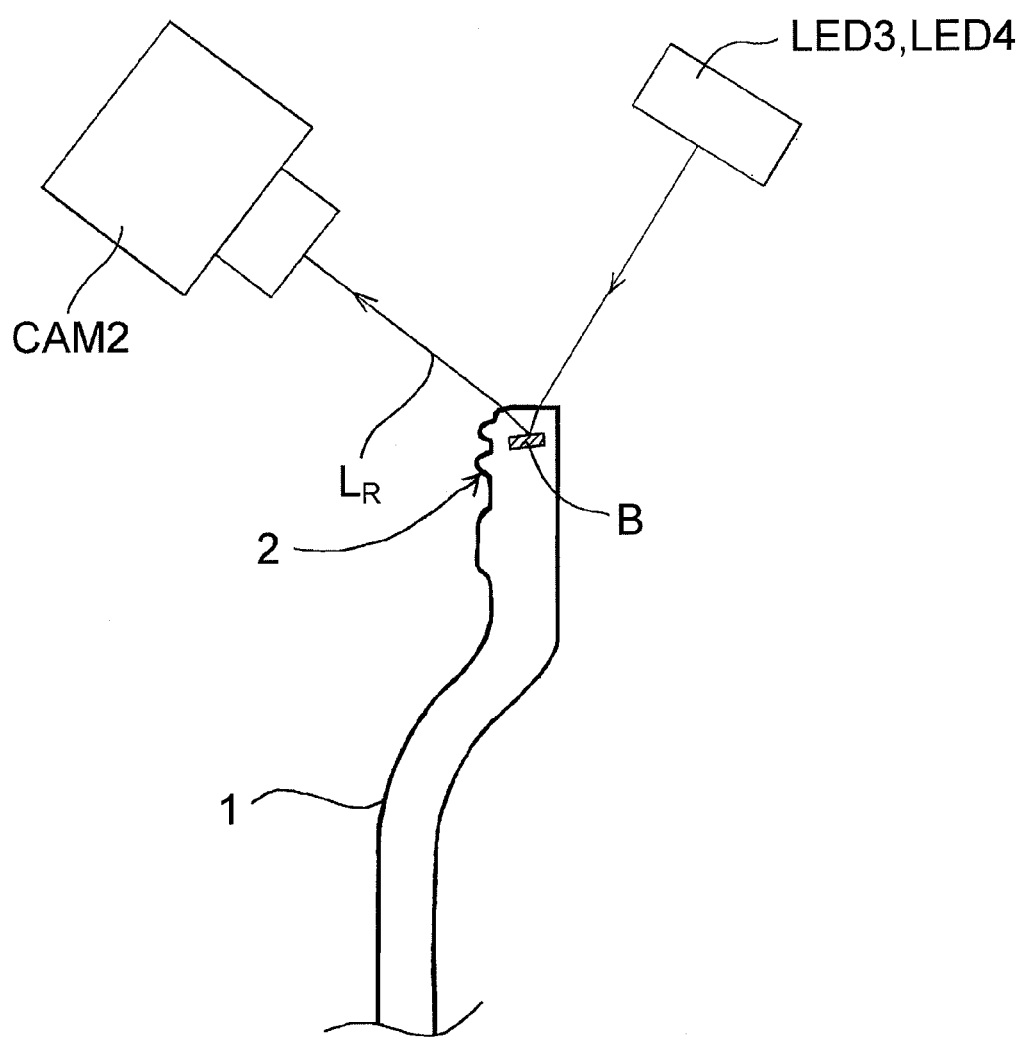
FIG. 3 is a schematic elevational view showing a path of light that is emitted from an illuminating unit, applied to the bottle-mouth portion of a glass bottle, and reflected from the bottle-mouth portion and imaged by a camera.

FIG. 3 is a schematic elevational view showing a path of light that is emitted from the illuminating unit LED3 or LED4, applied to the bottle-mouth portion 2 of the glass bottle 1, and reflected from the bottle-mouth portion 2 and captured by the camera CAM2. As shown in FIG. 3, the light that is emitted from the illuminating unit LED3 or LED4 is applied to the bottle-mouth portion 2 of the glass bottle 1. If the bottle-mouth portion 2 has a check B, then the light applied to the bottle-mouth portion 2 is reflected by the crack plane of the check B. The reflected light $L_R$ is imaged by the camera CAM2. In an image captured by the camera CAM2, an image area corresponding to the check B is brighter than other image areas of the image. The image processor of the controller 4 processes the image to detect the brighter image area and judges the brighter image area as a check.

The mechanism comprising a combination of the illuminating units LED1, LED2 and the camera CAM1 for capturing an image of a check in the bottle-mouth portion 2, and the mechanism comprising a combination of the illuminating units LED5, LED6 and the cameras CAM3, CAM4 for capturing an image of a check in the bottle-mouth portion 2 operate in the same manner as described above to apply a light to the check and image the light reflected from the crack plane of the check.

Figure 4:
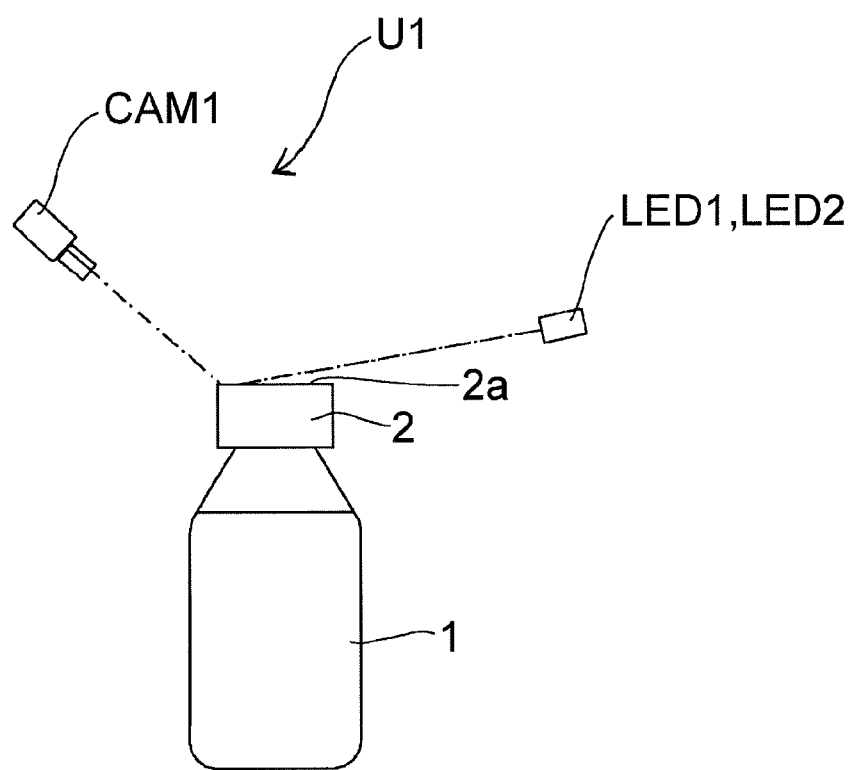
FIG. 4 is a schematic elevational view of a first inspection unit.
Figure 5:
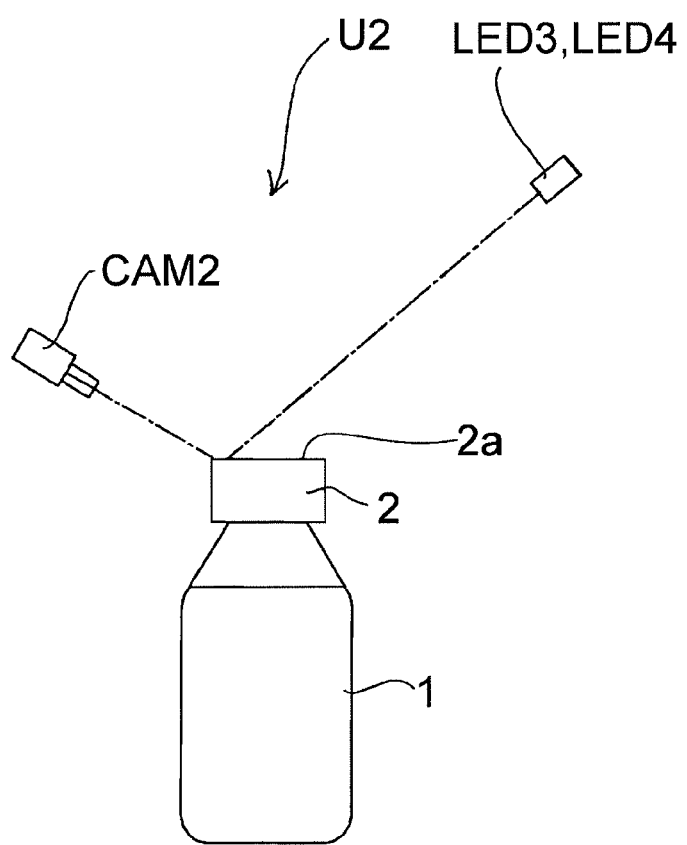
FIG. 5 is a schematic elevational view of a second inspection unit.
Figure 6:
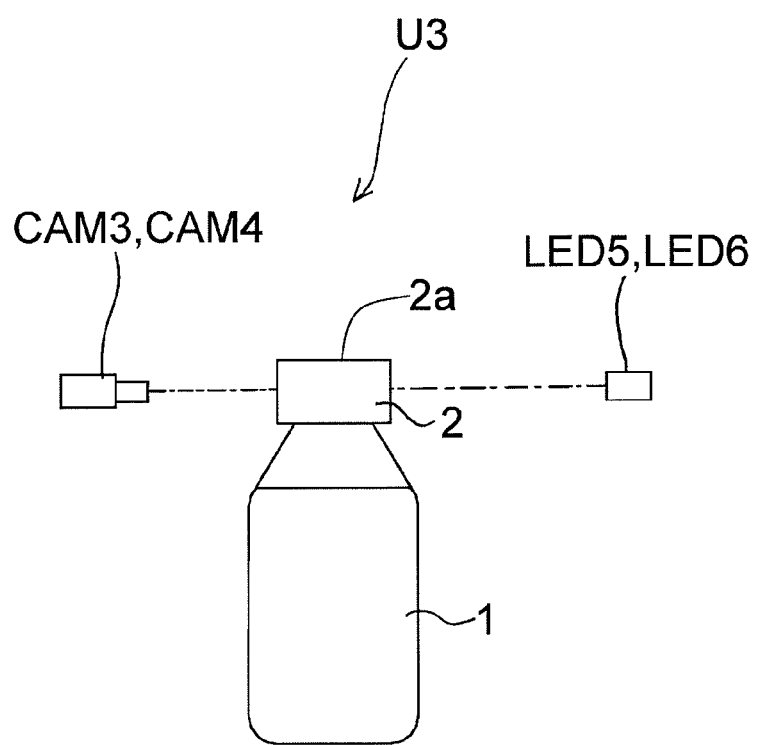
FIG. 6 is a schematic elevational view of a third inspection unit.

FIGS. 4 through 6 are schematic elevational views showing the layouts of the illuminating units LED1 through LED6 and the cameras CAM1 through CAM4 in the first, second, and third inspection units U1, U2, and U3 of the glass bottle inspection apparatus shown in FIGS. 1 and 2. In FIGS. 4 through 6, the bottle-mouth portion 2 is schematically illustrated.

FIG. 4 is a schematic elevational view of the first inspection unit U1. As shown in FIG. 4, the two illuminating units LED1, LED2 of the first inspection unit U1 are disposed in respective positions obliquely above the bottle-mouth portion 2 of the glass bottle 1 for illuminating the top surface 2a of the bottle-mouth portion 2 and the interior of the bottle-mouth. The camera CAM1 of the first inspection unit U1 is disposed in a position obliquely above the top surface 2a of the bottle-mouth portion 2 of the glass bottle 1 for capturing light from the top surface 2a of the bottle-mouth portion 2. The first inspection unit U1 having the above arrangement makes the camera CAM1 and the illuminating unit LED1 operate in cooperation with each other and also makes the camera CAM1 and the illuminating unit LED2 operate in cooperation with each other to capture an image of the top surface 2a, thereby detecting a check in the top surface 2a.

FIG. 5 is a schematic elevational view of the second inspection unit U2. As shown in FIG. 5, the two illuminating units LED3, LED4 of the second inspection unit U2 are disposed in respective positions obliquely above the bottle-mouth portion 2 of the glass bottle 1 for illuminating the top surface of the bottle-mouth portion 2 and the interior of the bottle-mouth. The camera CAM2 of the second inspection unit U2 is disposed in a position obliquely above a side face of the bottle-mouth portion 2 for capturing light from the top surface and the side face of the bottle-mouth portion 2. The second inspection unit U2 having the above arrangement makes the camera CAM2 and the illuminating unit LED3 operate in cooperation with each other and also makes the camera CAM2 and the illuminating unit LED4 operate in cooperation with each other to capture an image of the top surface 2a and the bottle-mouth side face including the thread 2n and the skirt 2s, thereby detecting a lateral check in the bottle-mouth portion 2.

FIG. 6 is a schematic elevational view of the third inspection unit U3. As shown in FIG. 6, the two illuminating units LED5, LED6 of the third inspection unit U3 are disposed in respective positions laterally of the bottle-mouth portion 2 of the glass bottle 1 for illuminating the bottle-mouth portion. The cameras CAM3, CAM4 of the third inspection unit U3 are disposed in respective positions laterally of a side face of the bottle-mouth portion 2 for capturing light from the side face of the bottle-mouth portion 2. The third inspection unit U3 having the above arrangement makes the camera CAM3 and the illuminating unit LED5 operate in cooperation with each other and also makes the camera CAM4 and the illuminating unit LED6 operate in cooperation with each other to capture an image of the bottle-mouth side face including the thread 2n and the skirt 2s, thereby detecting a vertical check in the bottle-mouth portion 2.

Figure 7:
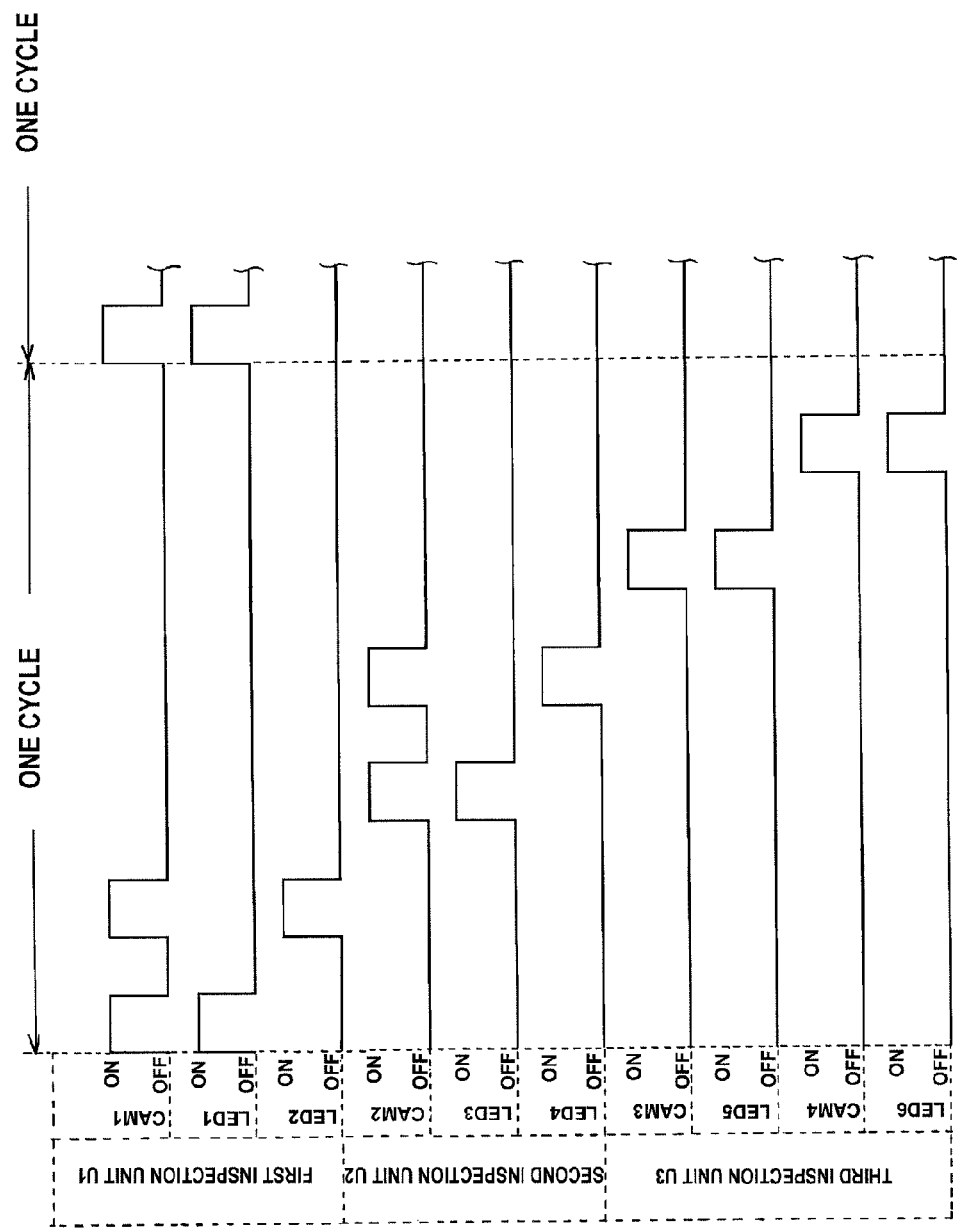
FIG. 7 is a timing chart showing operation timings of cameras CAM1 through CAM4 and illuminating units LED1 through LED6.

FIG. 7 is a timing chart showing operation timings of the cameras CAM1 through CAM4 and the illuminating units LED1 through LED6.

Each of the cameras CAM1 through CAM4 comprises a CCD camera. According to the present embodiment, the CCD camera is capable of forming several thousand images per second, for example. The illuminating units are turned on to emit pulsed lights based on an exposure time of the CCD camera. The cameras CAM1 through CAM4 and the illuminating units LED1 through LED6 are controlled by the controller 4. In FIG. 2, the controller 4 is shown as a unit that is separate from the cameras. However, the controller 4 may be incorporated in one of the cameras. If the controller 4 is incorporated in one of the cameras, then the camera having the controller 4 incorporated therein serves as a host device which also controls the image capturing timings of the other cameras.

As shown in FIG. 7, the camera CAM1 is first turned on (start of exposure), and the illuminating unit LED1 is turned on to emit a pulsed light at the same timing as the turning-on of camera CAM1. When image capturing by the camera CAM1 is completed, the camera CAM1 is turned off (end of exposure), and the illuminating unit LED1 is turned off at the same timing as the turning-off of camera CAM1. Thereafter, the camera CAM1 is turned on, and the illuminating unit LED2 is turned on to emit a pulsed light at the same timing as the turning-on of camera CAM1. When image capturing by the camera CAM1 is completed, the camera CAM1 is turned off, and the illuminating unit LED2 is turned off at the same timing as the turning-off of camera CAM1. Thereafter, the camera CAM2 is turned on, and the illuminating unit LED3 is turned on to emit a pulsed light at the same timing as the turning-on of camera CAM2. When image capturing by the camera CAM2 is completed, the camera CAM2 is turned off, and the illuminating unit LED3 is turned off at the same timing as the turning-off of camera CAM2. Then, the camera CAM2 is turned on, and the illuminating unit LED4 is turned on to emit a pulsed light at the same timing as the turning-on of camera CAM2. When image capturing by the camera CAM2 is completed, the camera CAM2 is turned off, and the illuminating unit LED4 is turned off at the same timing as the turning-off of camera CAM2. Thereafter, the camera CAM3 is turned on, and the illuminating unit LED5 is turned on to emit a pulsed light at the same timing as the turning-on of camera CAM3. When image capturing by the camera CAM3 is completed, the camera CAM3 is turned off, and the illuminating unit LED5 is turned off at the same timing as the turning-off of camera CAM3. Then, the camera CAM4 is turned on, and the illuminating unit LED6 is turned on to emit a pulsed light at the same timing as the turning-on of camera CAM4. When image capturing by the camera CAM4 is completed, the camera CAM4 is turned off, and the illuminating unit LED6 is turned off at the same timing as the turning-off of camera CAM4.

When image capturing by the camera CAM4 is completed and the camera CAM4 is turned off, one cycle of inspection process is finished. Subsequently, this cycle is repeated. During the repeated cycles, the bottle support 3 is rotated about its own axis to rotate the glass bottle 1 about its own axis $1x$. While the glass bottle 1 makes one revolution, the bottle-mouth portion 2 is imaged along its entire circumference by the cameras CAM1 through CAM4. A large number of images captured by the cameras CAM1 through CAM4 are successively processed by the image processor of the controller 4, and the full circumference of the top surface $2a$ of the bottle-mouth portion 2 and the full circumference of the bottle-mouth side face including the thread $2n$ and the skirt $2s$ are inspected to detect checks based on the processed images.

Figure 8:
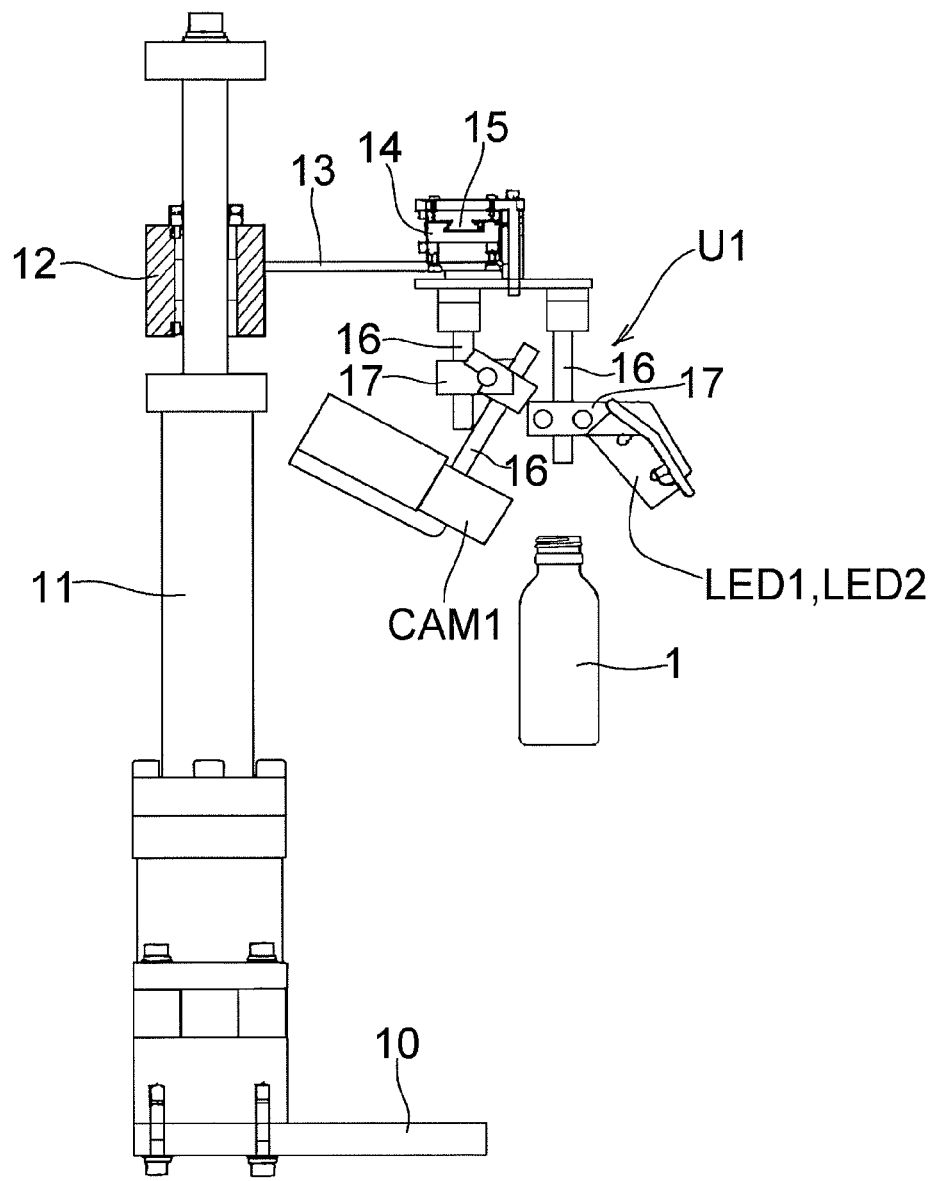
FIG. 8 is an elevational view showing a specific arrangement of an inspection unit.

FIG. 8 is an elevational view showing a specific arrangement of the inspection unit U1 of the glass bottle inspection apparatus according to the present invention.

The glass bottle 1 to be inspected is held by the inspection star wheel (not shown) and conveyed along the conveyance path on the circumference of the star wheel. The inspection unit U1 is disposed at a certain place in the conveyance path on the circumference of the star wheel.

As shown in FIG. 8, the inspection unit U1 has a support shaft 11 fixed to a frame 10 of the inspection apparatus, and a support member 12 vertically movably mounted on the support shaft 11. The two illuminating units LED1, LED2 and the camera CAM1 are supported on the support member 12 through a bracket 13. The illuminating units LED1, LED2 and the camera CAM1 are mounted on the bracket 13 by a slider mechanism including a guide rail 14 and a slider 15 and a slider mechanism including a plurality of guide rods 16 and a plurality of slider 17. The slider mechanisms allow the illuminating units LED1, LED2 and the camera CAM1 to be positionally adjustable vertically, horizontally, and obliquely with respect to the glass bottle 1 to be inspected.

The two illuminating units LED1, LED2 and the camera CAM1 can be detached from the inspection apparatus by removing the support member 12 from the support shaft 11. Therefore, the two illuminating units LED1, LED2 and the camera CAM1 can easily be replaced.

In the embodiment shown in FIGS. 1 through 8, two illuminating units are provided in combination with one camera, or one illuminating unit is provided in combination with one camera. However, three or more illuminating units may be provided in combination with one camera, and may be individually turned on to emit pulsed lights in synchronism with the image capturing timings of the camera.

Further, in the embodiment shown in FIGS. 1 through 8, a check in the bottle-mouth portion of a glass bottle is detected. However, the present invention is also applicable to the detection of a check in other locations, than the bottle-mouth portion, such as a bottom portion of a glass bottle.

In the above embodiment, a check which occurs in a glass bottle when it is produced is detected. Another defect which occurs in a glass bottle when it is produced is a blister. The blister is an air bubble that remains in a glass bottle, and is similar to a pore in a metal casting. Since, unlike a check, a blister is not a serious defect which may lead to a broken bottle, glass bottles with blisters may not be handled as defective products if appearance of the glass bottles is not important.

According to the present invention shown in FIGS. 1 through 8, illuminating units are disposed obliquely upwardly or laterally of the bottle-mouth portion of a glass bottle, and cameras are disposed obliquely upwardly or laterally of the bottle-mouth portion in combination with the illuminating units. Lights emitted from the illuminating units are applied to the bottle-mouth portion, and lights reflected from the crack plane of a check in the bottle-mouth portion are imaged by the cameras. Even if a blister is included as a defect in the bottle-mouth portion, lights reflected from an irregular curved surface at the boundary between the blister and the glass are applied to and imaged by the cameras. The inspection apparatus shown in FIGS. 1 through 8 is capable of detecting a check and a blister in the bottle-mouth portion as defects, but does not distinguish between a check and a blister.

The layout of illuminating units and cameras for detecting a check is limited generally to a one-to-one correspondence between the illuminating units and the cameras, as shown in FIGS. 1 through 6, because the crack plane of the check is generally planar and reflects lights in limited directions. The present inventors have found that a blister in a glass bottle has an irregular curved surface and hence reflects and scatters the incident light in various directions. As a result, it has been conceived that the blister can be detected using an illuminating unit dedicated for the detection of blister which is disposed at a position where the detection of checks is not affected.

Figure 9:
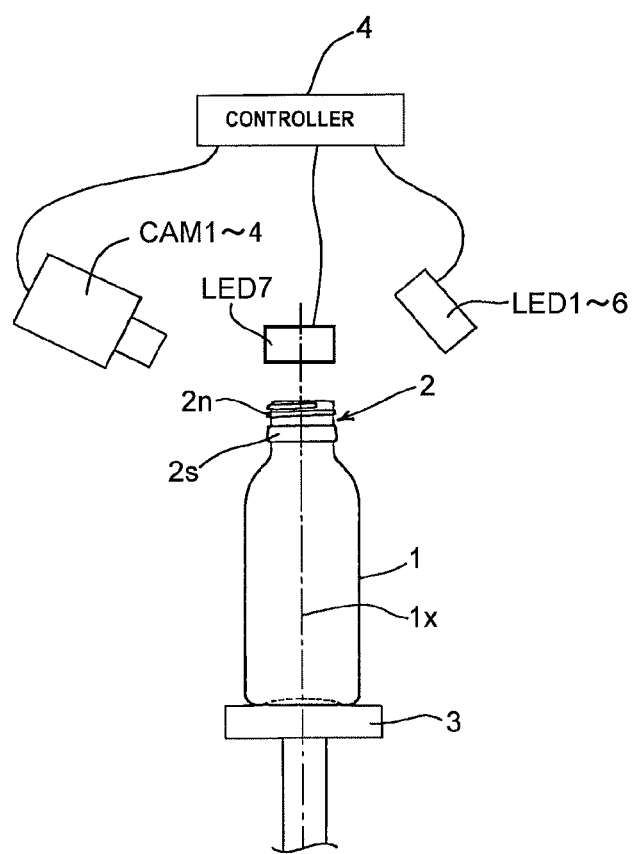
FIG. 9 is a schematic view of the glass bottle inspection apparatus shown in FIG. 2 to which an illuminating unit LED7 dedicated for the inspection of blisters is added.

FIG. 9 is a schematic view of the glass bottle inspection apparatus shown in FIG. 2 to which an illuminating unit LED7 dedicated for the inspection of blisters is added. As shown in FIG. 9, the illuminating unit LED7 dedicated for the inspection of blisters is disposed above the bottle-mouth portion 2 of the glass bottle 1. The illuminating unit LED7 is in the shape of a disk having a center aligned with the axis $1x$ of the glass bottle 1. The illuminating unit LED7 is connected to the controller 4, which controls the illuminating unit LED7 to emit a pulsed light. The illuminating units LED1 through LED6 and the cameras CAM1 through CAM4, which are positioned in the layout shown in FIG. 1, are illustrated not individually, but collectively in FIG. 9. The illuminating units LED1 through LED6 and the cameras CAM1 through CAM4 are connected to the controller 4, and controlled by the controller 4 to emit successive pulsed lights, and the cameras CAM1 through CAM4 are controlled by the controller 4 to capture successive images of the bottle-mouth portion 2, as is the case with the embodiment shown in FIG. 2. Since the illuminating unit LED7 is disposed above the bottle-mouth portion 2 of the glass bottle 1, when the illuminating unit LED7 is turned on to emit a pulsed light, the light reflected from a check in the bottle-mouth portion 2 is not applied to the cameras CAM1 through CAM4, and images captured by the cameras CAM1 through CAM4 include only an image area corresponding to a blister which may occur in the bottle-mouth portion 2.

Figure 10:
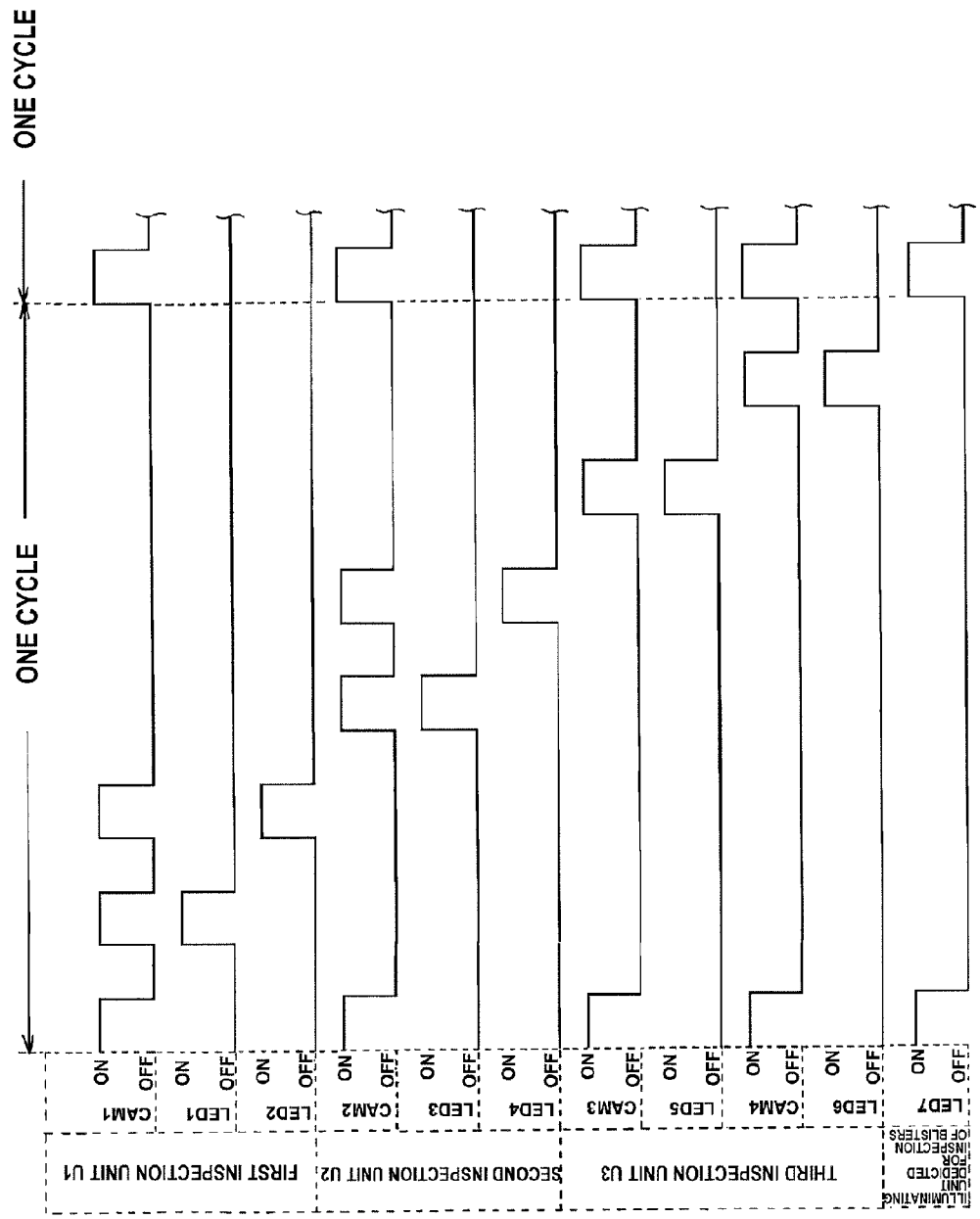
FIG. 10 is a timing chart showing operation timings of cameras CAM1 through CAM4 and illuminating units LED1 through LED6 illustrated in FIG. 7 to which operation timings of cameras CAM1 through CAM4 and an illuminating unit LED7 are added.

FIG. 10 is a timing chart showing operation timings of cameras CAM1 through CAM4 and illuminating units LED1 through LED6 illustrated in FIG. 7 to which operation timings of cameras CAM1 through CAM4 and an illuminating unit LED7 are added. As shown in FIG. 10, the cameras CAM1, CAM2, CAM3, CAM4 are turned on (start of exposure), and the illuminating unit LED7 is turned on to emit a pulsed light at the same timing as the turning-on of cameras CAM1, CAM2, CAM3, CAM4. When image capturing by the cameras CAM1, CAM2, CAM3, CAM4 is completed, the cameras CAM1, CAM2, CAM3, CAM4 are turned off (end of exposure), and the illuminating unit LED7 is turned off at the same timing as the turning-off of cameras CAM1, CAM2, CAM3, CAM4. Thereafter, the cameras CAM1 through CAM4 and the illuminating units LED1 through LED6 operate at the same timings as those shown in FIG. 7. As described in FIG. 7, when image capturing by the camera CAM4 is completed, the camera CAM4 is turned off and the illuminating unit LED6 is turned off at the same timing as the turning-off of camera CAM4, whereupon one cycle of inspection process is finished. Subsequently, the cycle is repeated. During the repeated cycles, the bottle support 3 is rotated about its own axis to rotate the glass bottle 1 about its own axis 1x. While the glass bottle 1 makes one revolution, the bottle-mouth portion 2 is imaged along its entire circumference by the cameras CAM1 through CAM4.

The images captured by the cameras CAM1 through CAM4 while the illuminating unit LED7 is turned on to emit a pulsed light do not include an image area corresponding to a check which may be present in the bottle-mouth portion 2, but include only an image area corresponding to a blister which may be present in the bottle-mouth portion 2. The captured images are successively processed by the image processor of the controller 4. If the processed images include a brighter image area in a dark background, then the image processor detects the brighter image area and judges it as a blister. Thereafter, the image processor masks the image area corresponding to the detected blister and removes the image area from an inspection area of the images captured by the cameras CAM1 through CAM4 while the illuminating units LED1 through LED6 are turned on to emit pulsed lights. If there is a brighter image area in the remaining inspection area of the captured images, then the image processor detects and judges the brighter image area as a check.

According to the present invention, the inspecting apparatus includes the illuminating unit LED7 dedicated for the inspection of blisters. A blister is detected from the images captured by the cameras CAM1 through CAM4 while the illuminating unit LED7 is turned on to emit a pulsed light, and the image area corresponding to the blister is masked and removed from an inspection area of the images captured by the cameras CAM1 through CAM4 while the illuminating units LED1 through LED6 are turned on to emit pulsed lights, so that only a check can be detected from the captured images. According to the present invention, therefore, a blister and a check can be detected distinguishably from each other.

Images may initially be captured by the cameras CAM1 through CAM4 while the illuminating units LED1 through LED6 are turned on to emit pulsed lights, and then a blister may be detected from images captured by the cameras CAM1 through CAM4 while the illuminating unit LED7 is turned on to emit a pulsed light. Thereafter, the image area corresponding to the blister may be masked and removed from an inspection area of the images captured by the cameras CAM1 through CAM4 while the illuminating units LED1 through LED6 are turned on to emit pulsed lights, so that only a check can be detected from the captured images.

In the embodiment shown in FIGS. 9 and 10, a blister in the bottle-mouth portion of a glass bottle is detected. However, the present invention is also applicable to the detection of a blister in other locations, than the bottle-mouth portion, such as a bottom portion of a glass bottle.

Although the embodiments of the present invention have been described above, the present invention is not limited to the above embodiments, but may be reduced to practice in various different conFIGurations within the scope of the technical concept thereof.

INDUSTRIAL APPLICABILITY

The present invention is applicable to a glass bottle inspection apparatus and method by detecting a defect at a specific location such as a bottle-mouth portion of a glass bottle by an imaging process.

REFERENCE SIGNS LIST

1 Glass bottle
1x Axis
2 Bottle-mouth portion
2a Top surface
2n Thread
2s Skirt
3 Bottle support
4 Controller
10 Frame
11 Support shaft
12 Support member
13 Bracket
14 Guide member
15, 17 Slider
16 Guide rod
CAM1 through CAM4 Camera
LED1 through LED7 Illuminating unit
U1 through U3 Inspection unit

The invention claimed is:

1. A glass bottle inspection apparatus comprising:
a first inspection unit which comprises plural illuminating units configured to illuminate a bottle-mouth portion of a glass bottle from an obliquely upward position and at least one camera configured to image light reflected from the glass bottle from an obliquely upward position;
a second inspection unit which comprises plural illuminating units configured to illuminate the bottle-mouth portion from a lateral position and at least one camera configured to image light reflected from the glass bottle from a lateral position, said second inspection unit being disposed below said first inspection unit;
a controller configured to control operations of said respective illuminating units and said respective cameras to detect a check in the bottle-mouth portion based on images captured by said camera of said first inspection unit and said camera of said second inspection unit;
wherein said controller controls said respective cameras so that an image capturing timing of said camera of said first inspection unit and an image capturing timing of said camera of said second inspection unit differ from each other;
said controller controls said plural illuminating units of said first inspection unit individually to emit a pulsed light in synchronism with the image capturing timing of said camera of said first inspection unit;
said controller controls said plural illuminating units of said second inspection unit individually to emit a pulsed light in synchronism with the image capturing timing of said camera of said second inspection unit; and
said controller detects a check which has a crack plane extending in a lateral direction in the bottle-mouth portion, based on the image captured by said camera of said first inspection unit, and detects a check which has a crack plane extending in a vertical direction in the bottle-mouth portion, based on the image captured by said camera of said second inspection unit.

2. A glass bottle inspection apparatus according to claim 1, wherein said plural illuminating units of said first inspection unit and said camera of said first inspection unit are disposed in respective positions which are substantially opposite to each other across the glass bottle.

3. A glass bottle inspection apparatus according to claim 1, further comprising:
a bottle support configured to support the glass bottle in an erected state and configured to rotate the glass bottle about its own axis.

4. A glass bottle inspection apparatus according to claim 1, wherein said plural illuminating units of said first inspection units and said plural illuminating units of said second inspection unit are disposed at different angular positions so as to surround the bottle-mouth portion of the glass bottle.

5. A glass bottle inspection apparatus according to claim 1, further comprising an illuminating unit dedicated for inspection of blisters which is disposed above the bottle-mouth portion;

wherein said controller controls said camera of said first inspection unit and said camera of said second inspection unit so as to image the bottle-mouth portion while said illuminating unit dedicated for inspection of blisters is turned on to emit a pulsed light; and said controller detects a blister in the bottle-mouth portion based on images captured while said illuminating unit dedicated for inspection of blisters is turned on to emit the pulsed light.

6. A glass bottle inspection apparatus according to claim 5, wherein said controller masks and removes an image area corresponding to the blister from an inspection area of the image captured while the illuminating units other than said illuminating unit dedicated for inspection of blisters are turned on to emit pulsed lights, and detects the check from the remaining inspection area.

7. A glass bottle inspection method of detecting a check in a bottle-mouth portion of a glass bottle by using a first inspection unit which comprises plural illuminating units configured to illuminate the bottle-mouth portion of the glass bottle from an obliquely upward position and at least one camera configured to image light reflected from the glass bottle from an obliquely upward position and a second inspection unit which comprises plural illuminating units configured to illuminate the bottle-mouth portion from a lateral position and at least one camera configured to image light reflected from the glass bottle from a lateral position, said second inspection unit being disposed below said first inspection unit, the glass bottle inspection method comprising:

controlling said respective cameras so that an image capturing timing of said camera of said first inspection unit and an image capturing timing of said camera of said second inspection unit differ from each other;

controlling said plural illuminating units of said first inspection unit individually to emit a pulsed light in synchronism with the image capturing timing of said camera of said first inspection unit;

controlling said plural illuminating units of said second inspection unit individually to emit a pulsed light in synchronism with the image capturing timing of said camera of said second inspection unit; and detecting a check which has a crack plane extending in a lateral direction in the bottle-mouth portion, based on the image captured by said camera of said first inspection unit, and detecting a check which has a crack plane extending in a vertical direction in the bottle-mouth portion, based on the image captured by said camera of said second inspection unit.

8. A glass bottle inspection method according to claim 7, wherein said plural illuminating units of said first inspection unit and said camera of said first inspection unit are disposed in respective positions which are substantially opposite to each other across the glass bottle.

9. A glass bottle inspection method according to claim 7, further comprising: rotating the glass bottle, supported in an erected state, about its own axis by a bottle support.

10. A glass bottle inspection method according to claim 7, wherein said plural illuminating units of said first inspection units and said plural illuminating units of said second inspection unit are disposed at different angular positions so as to surround the bottle-mouth portion of the glass bottle.

11. A glass bottle inspection method according to claim 7, further comprising:

controlling said camera of said first inspection unit and said camera of said second inspection unit so as to image the bottle-mouth portion while an illuminating unit disposed above the bottle-mouth portion and dedicated for inspection of blisters is turned on to emit a pulsed light; and detecting a blister in the bottle-mouth portion based on images captured while said illuminating unit dedicated for inspection of blisters is turned on to emit the pulsed light.

12. A glass bottle inspection method according to claim 7, further comprising: masking and removing an image area corresponding to the blister from an inspection area of the image captured while the illuminating units other than said illuminating unit dedicated for inspection of blisters are turned on to emit pulsed lights, and detecting the check from the remaining inspection area.

\* \* \* \* \*